(12) United States Patent
Avanzo et al.

(10) Patent No.: US 9,707,178 B2
(45) Date of Patent: Jul. 18, 2017

(54) PHARMACEUTICAL COMPOSITION

(75) Inventors: Matej Avanzo, Ljubljana (SI); Tanja Rozman Peterka, Ljubljana (SI); Igor Legen, Grosuplje (SI)

(73) Assignee: Lek Pharmaceuticals, d.d. (SI)

( * ) Notice: Subject to any disclaimer, the term of this patent is extended or adjusted under 35 U.S.C. 154(b) by 1007 days.

(21) Appl. No.: 12/299,237

(22) PCT Filed: May 2, 2007

(86) PCT No.: PCT/EP2007/003868
§ 371 (c)(1),
(2), (4) Date: Feb. 20, 2009

(87) PCT Pub. No.: WO2007/128478
PCT Pub. Date: Nov. 15, 2007

(65) Prior Publication Data
US 2009/0238871 A1    Sep. 24, 2009

(30) Foreign Application Priority Data

May 4, 2006 (EP) .................................... 06009223

(51) Int. Cl.
| A61K 9/36 | (2006.01) |
| A61K 9/20 | (2006.01) |
| A61K 31/4178 | (2006.01) |
| A61K 9/28 | (2006.01) |

(52) U.S. Cl.
CPC ........ *A61K 9/2013* (2013.01); *A61K 31/4178* (2013.01); *A61K 9/2018* (2013.01); *A61K 9/2054* (2013.01); *A61K 9/2866* (2013.01)

(58) Field of Classification Search
CPC .. A61K 9/2013; A61K 9/2018; A61K 9/2054; A61K 9/2866; A61K 31/4178
See application file for complete search history.

(56) References Cited

U.S. PATENT DOCUMENTS

| 5,081,109 A * | 1/1992 | Ulutin ..................... A61K 31/70 514/44 R |
| 6,555,139 B2 * | 4/2003 | Sharma .................. A61K 47/40 424/489 |
| 6,833,381 B2 * | 12/2004 | Ikeya .................. A61K 31/4184 514/397 |
| 6,878,703 B2 * | 4/2005 | Sada .................. A61K 31/4178 514/223.5 |
| 2006/0074117 A1 * | 4/2006 | Hedvati ............... C07D 405/14 514/381 |
| 2006/0089367 A1 * | 4/2006 | Bleicher .............. C07D 209/12 514/254.06 |
| 2006/0281800 A1 * | 12/2006 | Kumar et al. ................ 514/381 |
| 2007/0054948 A1 * | 3/2007 | Hedvati et al. ............... 514/381 |
| 2009/0131680 A1 * | 5/2009 | Zupancic et al. ............. 548/253 |

FOREIGN PATENT DOCUMENTS

| EP | 0503785 | 9/1992 | |
| EP | 1 604 664 A | 12/2005 | |
| EP | 1604664 A1 | 12/2005 | |
| JP | EP1604664 * | 12/2005 | ......... A61K 31/4422 |
| WO | WO-2005/42022 A2 | 5/2005 | |
| WO | WO 2005/042022 A2 | 5/2005 | |
| WO | WO-2006/00564 A1 | 1/2006 | |
| WO | WO 2006/000564 A1 | 1/2006 | |
| WO | WO 2006/029057 A | 3/2006 | |
| WO | WO-2006/29057 A1 | 3/2006 | |

OTHER PUBLICATIONS

Pai et al, 2013, Rasayan J. Chem, 6, 223-229.*
HR Brunner ("Brunner", J of Human Hypertension, 2002, 16, S13-S16).*
Nandini Pai and Seema Sawant, Synthesis of Olmesartan Acid Impurity of Olmesartan Medoxomil, Anti-Hypertensive Drug, 6 Rasayan J Chem. 223 (2013).*
Makoto Mizuno, et al, Pharmacology of CS-866, a Novel Nonpeptide Angiotensin II Receptor Antagonist, 285 Eur. J Pharmacol. 181 (1995).*
Olmesartan Medoxomil Properties II (2016).*
LV Allen: "Stearic Acid (in: Handbook of Pharmaceutical Excipients)"; Aug. 9, 2005, APHA Pharmaceutical Press, London, Chicago, p. 738.
LV Allen: Stearic Acid (in: Handbook of Pharmaceutical Excipients), Aug. 9, 2005, APHA Pharmaceutical Press, London, Chicag, p. 738.

* cited by examiner

*Primary Examiner* — Sean Basquill
(74) *Attorney, Agent, or Firm* — Luedeka Neely Group, P.C.

(57) ABSTRACT

A pharmaceutical composition comprising an ester of 4-(1-hydroxy-1-methylethyl)-2 propyl-1-[[2'-(1H-tetrazol-5-yl) [1,1'-biphenyl]-4-yl]methyl]-1H-imidazole-5-carboxylic acid characterized in that when exposed to 75% relative humidity at 40° in open dish for one month the total amount of related substances does not increase more than 1% is described.

34 Claims, No Drawings

PHARMACEUTICAL COMPOSITION

CROSS-REFERENCE TO RELATED APPLICATION

This application is a National Stage entry of International Application No. PCT/EP2007/003868, filed May 2, 2007, which claims priority to European Patent Application No. 06009223.6 filed May 4, 2006, the entire specification claims and drawings of which are incorporated herein by reference.

FIELD OF THE INVENTION

Present invention from the field of pharmaceutics relates to oral solid pharmaceutical composition containing olmesartan medoxomil, optionally in combination with hydrochlorothiazide.

BACKGROUND OF THE INVENTION

Olmesartan medoxomil, known from EP 503785, incorporated into a pharmaceutical composition may be used as an angiotenzin II antagonist. Chemically it is a 4-(1-hydroxy-1-methylethyl)-2 propyl-1-[[2'-(1H-tetrazol-5-yl)[1,1'-biphenyl]-4-yl]methyl]-1H-imidazole-5-carboxylic acid (5-methyl-2-oxo-1,3-dioxol-4-yl)methyl ester. Although olmesartan medoxomil is a prodrug that is hydrolyzed during absorption and it is marketed as Benicar or Olmetec in tablets for treatment of hypertension, it is not desirable that it hydrolyzes prior to ingestion.

DISCLOSURE OF THE INVENTION

In an aspect the invention provides a pharmaceutical composition comprising an ester of olmesartan.

An aspect of the invention is a pharmaceutical composition comprising an ester of olmesartan, preferably (5-methyl-2-oxo-1,3-dioxol-4-yl)methyl ester (olmesartan medoxomil) characterized in that when exposed to 75% relative humidity at 40° in open dish for one month the total amount of related substances does not increase more than 1%, preferably not more than 0.5% which means that total amount of related substances measured before and after said exposure will not differ for more than 1%, preferably not more than 0.5%; wherein this percentage is relative to the amount of olmesartan medoxomil before said exposure.

Specifically the invention is concerned with stabilization of a pharmaceutical composition, so it is in an aspect a composition comprising olmesartan medoxomil and 4-(1-hydroxy-1-methylethyl)-2 propyl-1-[[2'-(1H-tetrazol-5-yl)[1,1'-biphenyl]-4-yl]methyl]-1H-imidazole-5-carboxylic acid (olmesartan acid) characterized in that amount of olmesartan acid does not increase more than 0.3%, preferably not more than 0.2%, more preferably not more than 0.15% if exposed to 75% relative humidity at 40° in open dish for one month. The above increase means that difference of amount of olmesartan acid after said exposure and amount of olmesartan acid before said exposure will not be higher than said percentage, and this percentage is expressed relative to the amount of olmesartan medoxomil before said exposure.

In additional aspect the invention provides a stabilized pharmaceutical composition characterized in that amount of olmesartan acid does not increase more than 1% if exposed at room temperature to relative humidity 100% for 3 days, thereafter sealed and stored at 60° for one week.

The % amount increases can be in general determined by HPLC chromatography, and in specific embodiment is expressed as area %. Specifically can the amounts of increase be expressed as weight %, relative to starting weight of olmesartan medoxomil.

In order to achieve such stabilization the invention provides for use of stearic acid for manufacturing a pharmaceutical composition and in particular aspect it is a pharmaceutical composition comprising olmesartan medoxomil and stearic acid preferably in amounts 1% to 20%, more preferably 4% to 10% by weight of olmesartan medoxomil and from 0.1% to 1% by weight relative to weight of composition, specifically in amount from 0.2% to 0.8% by weight (preferred 0.4 to 0.7%, such as about 0.5% of stearic acid, or those two ingredients in ratios from 20:1 to 1:1, preferably from 8:1 to 3:1; the pharmaceutical composition may in an aspect further comprise one or more diluents, binders, and disintegrants and is in one embodiment made of cores, which are pellets, granules but preferably tablet cores which are preferably coated. Coating preferably comprises up to about 10% by weight of the composition, preferably from 1% to 5% and most preferably around 3%.

Specifically a pharmaceutical composition in accordance with our invention will comprise in cores: 4-10% by weight of the cores olmesartan medoxomil; 45-55% by weight of the cores lactose monohydrate; 15-25% by weight of the cores microcrystalline cellulose; 10-20% by weight of the cores low-substituted hydroxypropylcellulose; from 0.1% to 1%, specifically in amount from 0.2% to 0.8% by weight (preferred 0.4 to 0.7%, such as about 0.5% by weight of the cores of stearic acid. The invention is also embodied in the use of stearic acid for manufacturing a pharmaceutical composition comprising olmesartan medoxomil.

More specifically the coating applied to above cores will comprise 50-70% by weight of the coating of hydroxypropylmethylcellulose; 15-30 by weight of the coating titanium dioxide; 5-20% by weight of the coating talc and (optionally) pigments.

The industrial aspect of our invention provides a process for making a pharmaceutical composition comprising olmesartan medoxomil where each of the excipients being incorporated into a composition has a pH less than 8 if measured by a glass electrode in an aqueous solution or suspension containing 1 g of said excipient in 100 g of water at room temperature and also a process where above pharmaceutical composition is subsequently coated with a coating where an aqueous solution or suspension containing 1 g of coating in 100 g of water at room temperature has a pH less than 8 if measured by a glass electrode.

In an aspect of the invention the olmesartan medoxomil has particles size having d0.9<140 μm, and d0.5~50 μm, preferably d0.9 between 140 and 100 μm.

Further aspects of the invention are:

A pharmaceutical composition comprising an ester of 4-(1-hydroxy-1-methylethyl)-2 propyl-1-[[2'-(1H-tetrazol-5-yl)[1,1'-biphenyl]-4-yl]methyl]-1H-imidazole-5-carboxylic acid characterized in that when exposed to 75% relative humidity at 400 in open dish for one month the total amount of related substances does not increase more than 1%; specifically wherein the total amount of related substances does not increase from starting amount 0.2-0.6% by weight to more than 0.5-1.4% by weight.

A pharmaceutical composition comprising olmesartan medoxomil and olmesartan acid characterized in that amount of olmesartan acid does not increase more than 0.3% (in particular 0.2%) if exposed to 75% relative humidity at 40° in open dish for one month; specifically wherein the amount of olmesartan acid does not increase from starting amount 0.05-0.2% by weight to more than 0.2-0.5% by weight.

A pharmaceutical composition comprising olmesartan medoxomil and olmesartan acid, characterized in that amount of olmesartan acid does not increase more than 1% if exposed at room temperature to relative humidity 100% for 3 days, thereafter sealed and stored at 60° for one week; specifically wherein the amount of olmesartan acid does not increase from starting amount 0.05-0.2% by weight to more than 0.5-1.0% by weight.

A pharmaceutical composition in accordance with our invention, characterized in that amount of olmesartan acid does not increase more than 0.2% if sealed and stored at 60° for one week; specifically wherein the amount of olmesartan acid does not increase from starting amount 0.05-0.2% by weight to more than 0.2-0.4% by weight.

A pharmaceutical composition in accordance with our invention comprising olmesartan medoxomil where each of the constituents being incorporated into a composition has a pH less than 8 if measured by a glass electrode in an aqueous solution or suspension containing 1 g of said constituents in 100 g of water at room temperature; specifically comprising olmesartan medoxomil in amount 2% to 20% by weight and stearic acid in amount around from 0.1% to 1% by weight of the composition; more specifically wherein the amount of stearic acid is from 0.2% to 0.8% by weight of the composition, yet more specifically comprising in cores: 4-10% by weight of the cores olmesartan medoxomil; 45-55% by weight of the cores lactose monohydrate; 15-25% by weight of the cores microcrystalline cellulose; 10-20% by weight of the cores low-substituted hydroxypropylcellulose; and around 0.5% by weight of the cores stearic acid and where those cores are optionally coated.

A pharmaceutical composition comprising: 4-10% by weight olmesartan medoxomil; 45-55% by weight lactose monohydrate; 15-25% by weight microcrystalline cellulose; 10-20% by weight low-substituted hydroxypropylcellulose; from 0.1% to 1% by weight stearic acid, wherein said composition is optionally coated.

Any of pharmaceutical composition in accordance with our invention is in an aspect coated by a coating comprising 50-70% by weight of the coating of hydroxypropylmethylcellulose; 15-30 by weight of the coating titanium dioxide; 5-20% by weight of the coating talc and (optionally) one or more pigments, wherein the coating comprises up to 10% by weight of the composition.

A pharmaceutical composition in form of tablet core, pellet or granule comprising olmesartan medoxomil in amount 2% to 20% by weight of olmesartan or an ester thereof and stearic acid in amount below 1% by weight of the composition; specifically wherein an ester of olmesartan is olmesartan medoxomil and amount of stearic acid is from 0.1% to 0.9% by weight of the composition.

A pharmaceutical composition comprising olmesartan medoxomil and one or more pharmaceutically acceptable constituents where each of the constituents being incorporated into a composition has a pH less than 8 if measured by a glass electrode in an aqueous solution or suspension containing 1 g of said constituents in 100 g of water at room temperature.

The pharmaceutical composition according to previous claim comprising olmesartan medoxomil in amount 2% to 20% by weight wherein one of constituents is a stearic acid in amount 0.1 to 5% by weight of the composition.

The pharmaceutical composition according to previous claim comprising olmesartan medoxomil in amount 2% to 20% by weight wherein one of constituents is a stearic acid in amount 0.1 to 0.9% by weight of the composition.

A process for making a pharmaceutical composition comprising olmesartan medoxomil where each of the constituents being incorporated into a composition has a pH less than 8 if measured by a glass electrode in an aqueous solution or suspension containing 1 g of said constituents in 100 g of water at room temperature; specifically where pharmaceutical composition is in form of tablet core, pellet or granule; more specifically where pharmaceutical composition is subsequently coated with a coating where an aqueous solution or suspension containing 1 g of coating in 100 g of water at room temperature has a pH less than 8 if measured by a glass electrode.

Use of stearic acid in amount by weight from 0.1 to 1% (which means more than 0.1% and less than 1% by weight relative to the weight of the finished composition), in particular from 0.1 to 0.9%, more particular from 0.1 to 0.8% for manufacturing a pharmaceutical composition comprising olmesartan medoxomil.

Use of stearic acid in amount from 0.1 to 1% for manufacturing a pharmaceutical composition comprising olmesartan medoxomil to prevent degradation of olmesartan medoxomil to olmesartan acid.

Use of stearic acid (specifically in weight amount relative to the weight of the composition from 0.1 to 1%) for manufacturing a pharmaceutical composition comprising olmesartan medoxomil wherein olmesartan medoxomil has particles size having d0.9<140 µm, and d0.5~50 µm, more specifically wherein olmesartan medoxomil has particles size d0.9 between 140 and 100 µm and especially specifically with smaller particle sizes d0.9<140 µm and d0.5<80 µm, or even smaller, having d0.5<70 µm or having d0.5<50 µm.

DETAILED DESCRIPTION OF THE INVENTION

We have discovered that bulk olmesartan medoxomil, is most stable in the pH range 3-5. The main degradation product is olmesartan acid. Olmesartan medoxomil almost completely hydrolyzes at basic conditions. In a solution at pH=7 the amount of formed olmesartan acid increases by 0.5% in 24 hours, while in 1M HCl the amount increases by approximately 6%. The amounts of individual and total impurities are measured in area % and determined by HPLC using the following procedure: a sample solution was prepared by diluting quantity of pulverized tablet equivalent to 25 mg of olmesartan medoxomil in 50 ml volumetric flask to volume with diluent (Eluent A+Eluent B=50%/50%). Column Waters Xbridge C18, 150×4.6 mm, 3.5 µm was used and eluted by Eluent A (0.025 M $KH_2PO_4$ adjusted to pH=2.5 with 50% $H_3PO_4$) and Eluent B (acetonitrile) with following gradient: A:B=100:0, from 15 to 30 minutes A:B=70:30, after 30 min A.B=0:100. Flow rate was 1 m/min, Injection volume was 20 µl, column temperature was 30° C., detection wavelength at 225 nm.

Related substances preferably mean those structurally similar compounds and/or degradation products (impurities) having retention factors at approximately 0.31 (olmesartan acid); 1.23; 1.37; 1.41; 1.64; and 2.55 as analysed by above procedure. The total amount of related substances means the sum of area % of individual impurities, preferably those at above retention factors, each having an area % equal or higher to 0.03%.

Tablets on the market only partially stabilize olmesartan medoxomil, it is known, that they contain around 0.3% of olmesartan acid. The amount of this substance in marketed Olmesartan medoxomil tablets (Benicar) after they have been stored for 1 month at 40° C. at 75 relative humidity increases in tablets protected in alu-alu blister by around 0.15% while in PVC/PVDC packaging even by around 0.45% (the data provided is expressed as area %; response factor (Rf) of olmesartan acid 1.25, and 1 for other impurities relative to olmesartan can be used for calculations to get weight %), while in unprotected tablets in open dish increases by 1.3%. By exposing the tablets on market initially containing 0.3% of olmesartan acid, after one week in dry atmosphere at 60° C. the amount of this substance is 0.7% while in humid atmosphere at 60° C. it is 3.5% (total amount of related substances: 3.9%).

We have found that by carefully choosing the tableting excipients, we are able to manufacture stable pharmaceutical compositions comprising Olmesartan medoxomil.

The composition may be prepared by preferably using as diluents: lactose or microcrystalline cellulose; but also silicified microcrystalline cellulose, powdered cellulose, calcium sulphate dihydrate, carboxymethylcellulose calcium, cellulose acetate, ethylcellulose, dextrin, glucose, fructose, maltodextrin, kaolin, maltitol, sucrose, sodium chloride, starch, pregelatinized starch, polymethacrylates, sorbitol, etc; as binders preferably microcrystalline cellulose and low substituted HPC, but also starch, pregelatinized starch, gelatine, sodium carboxymethylcellulose, methylcelullose, hydroxyethylcelullose, hydroxypropycellulose (HPC), hydroxypropylmethylcellulose, polyvinylpyrolidone, alginic acid, sodium alginate, dextrin, maltodextrin, carbomer, polymethacrilates, etc; as desintegrants likewise preferably microcrystalline cellulose and low substituted HPC but also starch, pregelatinized starch, carboxymethylcellulose sodium, cross-linked carboxymethylcellulose, cellulose powdered, carboxymethylcellulose calcium, methylcellulose, silicified microcrystalline cellulose, polacrilin potassium (Amberlit), cross-linked polyvinylpyrolidone, colloidal silicon dioxide, alginic acid, etc. As lubricant and glidant, stearic acid is preferably used as opposed to other more alkaline lubricants and binders. Additionally other lubricants can be used such as polyethylene glycols, (light) mineral oils, canola oil, sodium benzoate, etc.

Surprisingly stearic acid used in amount from 0.1% to 1% by weight relative to weight of composition, specifically in amount from 0.2% to 0.8% by weight (preferred 0.4 to 0.7%, such as about 0.5%) successfully stabilizes the solid oral pharmaceutical composition containing olmesartan medoxomil, optionally in combination with hydrochlorothiazide. The amount used is much lower than routinely used in pharmaceutical compositions, as for example taught by Handbook of Pharmaceutical Excipinets.

In general we observed a best stabilization where each of the constituents being incorporated into a composition has a pH less than 9, preferably less than 8; but can have pH above 5. A constituent may be a single inactive ingredient (excipient) or another active or a mixture of excipients (if such mixture is separately prepared and subsequently combined with olmesartan medoxomil). We have concluded that the excipients, being in contact with olmesartan medoxomil, being incorporated into a composition should preferably have a pH less that 8 if measured by a glass electrode in an aqueous solution or suspension containing 1 g of said excipient in 100 g of water at room temperature. Thus the pH of excipents uses in examples is as follows; lactose: about 5.2, L-HPC: about 6.7, MCC: about 6.7, stearic acid: about 5.4, Mg stearate: about 9.5, coating suspension (Example 3): about 6.6.

Preferably the composition is prepared as follows: lactose monohydrate and olmesartan medoxomil are mixed and sieved. Low-substituted hydroxypropylcellulose (L-HPC) and microcrystalline cellulose are added and the blend is mixed and sieved. At the end the stearic acid is added. The obtained mixture is blended for a short time and compressed into tablets. Onto those tablets a coating may be applied as follows: hydroxypropylmethylcellulose, talc, titanium dioxide and optionally hydroxypropylcellulose and/or iron oxide and/or polyethyleneglycol are dispersed in water. Coating may, for example, protect the tablet cores from light, or provide for taste masking. Tablet cores are coated with obtained water dispersion to defined weight and upon drying polished with talc.

The preferred ratios (given for cores as % of coated tablet and for coating as (% of dry film coat) of substances to be used in manufacturing the pharmaceutical composition in accordance with our invention are:

| TABLET CORE | |
|---|---|
| Olmesartan medoxomil | 4-10% |
| Lactose monohydrate spray dried | 45-55% |
| Microcrystalline cellulose (preferred Avicel PH 102) | 15-25% |
| Low-Substituted Hydroxypropyl Cellulose (pref. L-HPC LH11) | 10-20% |
| Stearic Acid | 0.1-1% |
| COAT | |
| Hydroxypropylmethylcellulose (preferred Pharmacoat 606 ®) | 40-70% |
| Talc | 5-20% |
| Titanium Dioxide | 15-30% |
| Hydroxypropycellulose (preferred Klucel EF ®) | 0-20% |
| Iron Oxide | 0-10% |
| Polyethylene glycol 400 | 0-15% |

In one of the preferred embodiments the coating will comprise HPMC, talc and titanium dioxide in ratios: 50-70:5-20:15-30 and the other: HPMC, HPC. PEG, talc and titanium dioxide in ratios: 40-60:10-20:5-15:5-15:20-30.

By exposing so prepared tablets (Example 1) initially containing 0.12% of olmesartan acid, after one week in dry atmosphere at 60° C. the amount of this substance is 0.24% while in humid atmosphere (that is: after being exposed to 100% relative humidity at room temperature for 3 days and thereafter sealed, i.e put in water tight container) at 60° C. it is 0.52%. The total amount of related substances being 0.58% and 0.89% respectively. At 40° C. at 75% relative humidity in open dish the amount of said substance was after one month 0.32%, while the total amount of related substances was 0.66%.

We compared the stability of those tablets to those where stearic acid has been replaced by more commonly used lubricant Mg stearate (example 2) and discovered that so prepared tablets again initially contain 0.12% of olmesartan acid, however after one week in dry atmosphere at 60° C. the amount of this substance is already 0.41% while in humid atmosphere at 60° C. it is 2.34%. The total amount of related substances being 0.79% and 2.81% respectively. At 40° C. at 75% relative humidity in open dish the amount of said substance was after one month 0.88%, while the total amount of related substances was 1.35%.

Results are presented in following table

| | | Storage condition Container closure | | | |
|---|---|---|---|---|---|
| | | / | 60° C. sealed vials | *humid atm + 60° C. vials | 40° C./ 75% open dish |
| | | | | Time | |
| | | 0 | 1 week | 1 week | 1 month |
| Olmesartan acid impurity [%] | Example 1 | 0.12 | 0.24 | 0.52 | 0.32 |
| | Example 2 | 0.12 | 0.41 | 2.34 | 0.88 |
| | Benicar® | 0.35 | 0.68 | 3.47 | 1.65 |
| Total impurities [%] | Example 1 | 0.47 | 0.58 | 0.89 | 0.66 |
| | Example 2 | 0.46 | 0.79 | 2.81 | 1.35 |
| | Benicar® | 0.55 | 0.98 | 3.94 | 2.00 |

Results of increase of olmesartan acid, and total impurities in a solid oral solid pharmaceutical composition containing olmesartan medoxomil, optionally in combination with hydrochlorothiazide according to our invention are presented in following Table (in parenthesis the particular preferred values)

| | | Storage condition | | |
|---|---|---|---|---|
| Increase of | Starting amount | 60° C. sealed vials 1 week | *humid atm + 60° C. Container closure vials 1 week | 40° C./75% open dish 1 month |
| Olmesartan acid impurity [%] | 0.01-0.25 (0.05-0.2) | 0.1-0.6 (0.2-0.4) | 0.3-1.2 (0.5-0.9) | 0.1-1.0 (0.2-0.5) |
| Total impurities [%] | 0.2-0.8 | 0.4-0.9 (0.5-0.7) | 0.4-2.0 (0.5-1.2) | 0.5-1.4 (0.6-1.2) |

Thus for example a pharmaceutical composition comprising an ester of 4-(1-hydroxy-1-methylethyl)-2 propyl-1-[[2'-(1H-tetrazol-5-yl)[1,1'-biphenyl]-4-yl]methyl]-1H-imidazole-5-carboxylic acid in accordance with our invention is characterized in that when exposed to 75% relative humidity at 40° in open dish for one month the total amount of related substances does not increase more than 1%, in particular will not increase from starting amount 0.2-0.6% by weight to more than 0.5-1.4% by weight.

in another embodiment the pharmaceutical composition in accordance with our invention comprising olmesartan medoxomil and olmesartan acid is characterized in that amount of olmesartan acid does not increase more than 0.3% if exposed to 75% relative humidity at 40° in open dish for one month, in particular will not increase from starting amount 0.05-0.2% by weight to more than 0.2-0.5% by weight.

It is generally convenient that the pharmaceutical composition comprising olmesartan medoxomil will release the active pharmaceutical ingredient rapidly, that is to have a fast dissolution because the olmesartan medoxomil as such is a prodrug and it not desirable that it undergoes extensive hydrolysis before entering into bloodstream. Thus we have designed the coating not to substantially influence the dissolution characteristics.

We have also discovered that particle size distribution of olmesartan medoxomil used in preparing a composition influences the dissolution characteristics. Thus we have tested similar compositions having incorporated olmesartan medoxomil having different particle sizes distributions and found that satisfactory dissolutions are achieved with particle sizes having d0.9<140 µm, and d0.5~50 µm, preferably d0.9 between 140 and 100 µm while decreasing the particle sizes by micronization to d0.9~10 µm did not have an effect.

Satisfactory dissolution means that when subjecting tablets to dissolution test according to USP, using Apparatus 2 (paddle) at 50 rpm with 1000 ml of phosphate buffer (50 mM) at pH 6.8 and 37° C.; more than 80% of olmesartan medoxomil is released after 30 minutes, which can be conveniently measured by HPLC.

On the other hand, we have discovered that the effect of stabilization is comparable when using stearic acid and magnesium stearate in case of larger particle sizes, having d0.9>140 µm, and d0.5>50 µm, however in case of smaller particle sizes, in particular having d0.9<140 µm and in particular d0.5<70 µm, stability of compositions comprising stearic acid is better.

The invention is illustrated in more detail by the following non-limiting examples. The weights are given for single tablet, however skilled person may multiply those values and produce batches of tablets: Examples show the effect of amount of added stearic acid from 0.2% (Example 4) to 0.7% (Example 3).

Example 1

220 mg lactose monohydrate and 40 mg olmesartan medoxomil are mixed and sieved through 0.5 mm sieve. Thereto 70.4 mg low-substituted hydroxypropylcellulose (L-HPC) and 94.5 mg microcrystalline cellulose are added and the blend is mixed and sieved through 0.5 mm sieve again. At the end 2.14 mg of stearic acid, sieved through 0.3 mm sieve, is added. The obtained mixture is blended for a short time and compressed into tablet with mass 427 mg. Onto this tablet a coating is applied as follows: 5.5 mg of hydroxypropylmethylcellulose (Pharmacoat 606), 2.5 mg of hydroxypropylcellulose (Klucel EF), 2.7 mg of titanium dioxide, 1.3 mg PEG 400 and 1.0 mg of talc are dispersed in water. The tempered tablet core is coated with obtained water dispersion to defined weight 440 mg and upon drying polished with talc.

Example 2

220 mg lactose monohydrate and 40 mg olmesartan medoxomil are mixed and sieved through 0.5 mm sieve. Thereto 70.4 mg L-HPC and 94.5 mg microcrystalline cellulose are added and the blend is mixed and sieved through 0.5 mm sieve again. At the end 2.14 mg of Mg stearate, sieved through 0.3 mm sieve, is added. The obtained mixture is blended for a short time and compressed into tablet with mass 427 mg. Onto this tablet a coating is applied as follows: 5.5 mg of hydroxypropylmethylcellulose (Pharmacoat 606), 2.5 mg of hydroxypropylcellulose (Klucel EF), 2.7 mg of titanium dioxide, 1.3 mg PEG 400 and 1.0 mg of talc are dispersed in water. The tempered tablet core is coated with obtained water dispersion to defined weight 440 mg and upon drying polished with talc.

Example 3

Per tablet 222 mg lactose monohydrate and 40 mg micronized olmesartan medoxomil are mixed and sieved through 0.5 mm sieve. Thereto 70.4 mg L-HPC and 94.5 mg microcrystalline cellulose are added and the blend is mixed and sieved through 0.5 mm sieve again. At the end 3.0 mg of stearic acid, sieved through 0.3 mm sieve, is added. The obtained mixture is blended for a short time and compressed into tablet with mass 430 mg. Onto this tablets a coating is applied as follows: 6.6 mg of hydroxypropylmethylcellulose (Pharmacoat 606), 2.7 mg of titanium dioxide and 1.3 mg of talc are dispersed in water. The tempered tablet core is coated with obtained water dispersion to defined weight 440 mg and upon drying polished with talc. The stability result are better than preceding example and similar to example 1.

Example 4

Per tablet 440 mg lactose monohydrate and 80 mg micronized olmesartan medoxomil are mixed and sieved through 0.5 mm sieve. Thereto 140 mg L-HPC and 190 mg microcrystalline cellulose are added and the blend is mixed and sieved through 0.5 mm sieve again. At the end 2 mg of stearic acid, sieved through 0.3 mm sieve, is added. The obtained mixture is blended for a short time and compressed into tablet with mass 852 mg. Onto this tablets a coating is applied as follows: 13 mg of hydroxypropylmethylcellulose (Pharmacoat 606), 5 mg of titanium dioxide and 2.6 mg of talc are dispersed in water. The tempered tablet core is coated with obtained water dispersion to defined weight 870 mg and upon drying polished with talc. The stability result are comparable to example 1.

The invention claimed is:

1. A pharmaceutical composition comprising olmesartan medoxomil having a particle size wherein d(0.9) is less than 140 μm, more than 0.1% and less than 1% by weight stearic acid, and degradation products of olmesartan medoxomil that include, but are not limited to, olmesartan acid,
   wherein olmesartan medoxomil and degradation products of olmesartan medoxomil are the only active ingredients in the pharmaceutical composition
   wherein each of the constituents incorporated into said composition has a pH less than 8 if measured by a glass electrode in an aqueous solution or suspension containing 1 g of said constituents in 100 g of water at room temperature, and
   wherein the pharmaceutical composition is coated with a coating where an aqueous solution or suspension containing 1 g of coating in 100 g of water at room temperature has a pH less than 8 if measured by a glass electrode; and
   wherein when the pharmaceutical composition is exposed to 75% relative humidity at 40° C. in an open dish for one month, the total amount of degradation products of olmesartan medoxomil does not increase more than 1%, and the amount of olmesartan acid does not increase more than 0.3%.

2. The pharmaceutical composition according to claim 1 wherein the total amount of related substances increases from a starting amount of 0.2-0.6% by weight, to not more than 0.5-1.4% by weight.

3. The pharmaceutical composition according to claim 1, comprising olmesartan medoxomil and olmesartan acid characterized in that the amount of olmesartan acid does not increase more than 0.3% if exposed to 75% relative humidity at 40° C. in an open dish for one month.

4. The pharmaceutical composition according to claim 1, wherein the amount of olmesartan acid increases from a starting amount of 0.05-0.2% by weight, to not more than 0.2-0.5% by weight.

5. The pharmaceutical composition according to claim 1, characterized in that the amount of olmesartan acid does not increase more than 1% if exposed at room temperature to relative humidity of 100% for 3 days, and thereafter sealed and stored at 60° C. for one week.

6. The pharmaceutical composition according to claim 1, wherein the amount of olmesartan acid increases from a starting amount of 0.05-0.2% by weight, to not more than 0.5-1.0% by weight.

7. A pharmaceutical composition comprising an ester of olmesartan having a particle size wherein d(0.9) is less than 140 μm, olmesartan acid and more than 0.1% and less than 1% by weight stearic acid, wherein each of the constituents incorporated into said composition has a pH less than 8 if measured by a glass electrode in an aqueous solution or suspension containing 1 g of said constituents in 100 g of water at room temperature,
   wherein the ester of olmesartan and olmesartan acid are the only active ingredients in the pharmaceutical composition,
   wherein the pharmaceutical composition is coated with a coating where an aqueous solution or suspension containing 1 g of coating in 100 g of water at room temperature has a pH less than 8 if measured by a glass electrode, and
   wherein the amount of omesartan acid detected in an assay does not increase more than 0.2% when the pharmaceutical composition is sealed and stored at 60° C. for one week.

8. The pharmaceutical composition according to claim 7, wherein the amount of olmesartan acid increases from a starting amount of 0.05-0.2% by weight, to not more than 0.2-0.4% by weight.

9. The pharmaceutical composition according to claim 1 comprising olmesartan medoxomil in an amount of from 2% to 20% by weight and stearic acid in an amount of more than 0.1% and less than 1% by weight of the composition.

10. The pharmaceutical composition according to claim 9, wherein the amount of stearic acid is from 0.2% to 0.8% by weight of the composition.

11. The pharmaceutical composition according to claim 10 comprising in cores: 4-10% by weight of the cores olmesartan medoxomil; 45-55% by weight of the cores lactose monohydrate; 15-25% by weight of the cores microcrystalline cellulose; 10-20% by weight of the cores low-substituted hydroxypropylcellulose; and about 0.5% by weight of the cores stearic acid.

12. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose;

10-20% by weight low-substituted hydroxypropylcellulose; more than 0.1% and less than 1% by weight stearic acid; and olmesartan medoxomil degradation products comprising olmesartan acid, wherein olmesartan medoxomil and olmesartan medoxomil degradation products comprising olmesartan acid are the only active ingredients in the pharmaceutical composition, wherein said composition is optionally coated, wherein each of the constituents incorporated into said composition has a pH less than 8 if measured by a glass electrode in an aqueous solution or suspension containing 1 g of said constituents in 100 g of water at room temperature, and wherein the amount of olmesartan acid does not increase more than 0.3% if exposed to 75% relative humidity at 40° C. in an open dish for one month.

13. The pharmaceutical composition according to claim 12 which is coated by a coating comprising 50-70% by weight of the coating of hydroxypropylmethylcellulose; 15-30% by weight of the coating titanium dioxide; 5-20% by weight of coating talc; and optionally one or more pigments, wherein the coating comprises up to 10% by weight of the composition.

14. A pharmaceutical composition in form of tablet core, pellet, or granule comprising olmesartan medoxomil having a particle size wherein $d(0.9)$ is less than 140 μm in an amount of from 2% to 20% by weight, stearic acid in amount below 1% by weight of the composition, and olmesartan medoxomil degradation products comprising olmesartan acid, wherein olmesartan medoxomil and olmesartan medoxomil degradation products comprising olmesartan acid are the only active ingredients in the pharmaceutical composition, wherein each of the constituents being incorporated into said composition has a pH less than 8 if measured by a glass electrode in an aqueous solution or suspension containing 1 g of said constituents in 100 g of water at room temperature, and wherein an amount of olmesartan acid does not increase more than 0.3% if exposed to 75% relative humidity at 40° C. in an open dish for one month.

15. The pharmaceutical composition according to claim 14 wherein an ester of olmesartan is olmesartan medoxomil and the amount of stearic acid is from 0.1% to 0.9% by weight of the composition.

16. A pharmaceutical composition comprising olmesartan medoxomil having a particle size wherein $d(0.9)$ is less than 140 μm, stearic acid in an amount of from 0.1 to 1% by weight of the composition, and olmesartan medoxomil degradation products comprising olmesartan acid, and one or more pharmaceutically acceptable excipients, wherein olmesartan medoxomil and olmesartan medoxomil degradation products comprising olmesartan acid are the only active ingredients in the pharmaceutical composition, wherein each of the constituents incorporated into the pharmaceutical composition has a pH less than 8 if measured by a glass electrode in an aqueous solution or suspension containing 1 g of said constituents in 100 g of water at room temperature, and wherein the pharmaceutical composition is coated with a coating, and wherein an amount of olmesartan acid does not increase more than 0.3% if exposed to 75% relative humidity at 40° C. in an open dish for one month.

17. The pharmaceutical composition according to claim 16 comprising olmesartan medoxomil in an amount of from 2% to 20% by weight, and a stearic acid in an amount of from 0.1 to 0.9% by weight of the composition.

18. A process for making a pharmaceutical composition comprising olmesartan medoxomil having a particle size of $d0.9<140$ μm and stearic acid in an amount of from 0.1 to 1% by weight of the composition, the process comprising incorporating various constituents where each of the constituents has a pH less than 8 if measured by a glass electrode in an aqueous solution or suspension containing 1 g of said constituents in 100 g of water at room temperature and wherein the pharmaceutical composition is subsequently coated with a coating where an aqueous solution or suspension containing 1 g of coating in 100 g of water at room temperature has a pH less than 8 if measured by a glass electrode.

19. A process according to claim 18, where the pharmaceutical composition is in the form of tablet core, pellet or granule.

20. A process according to claim 19, where the pharmaceutical composition is subsequently coated with a coating where an aqueous solution or suspension containing 1 g of coating in 100 g of water at room temperature has a pH less than 8 if measured by a glass electrode.

21. The process of claim 18 wherein stearic acid is incorporated into the pharmaceutical composition in an amount more than 0.1% and less than 1% by weight relative to the weight of the finished composition.

22. The process according to claim 21 wherein the amount of stearic acid is around 0.5%.

23. A method of preventing olmesartan medoxomil from degrading into olmesartan acid, the method comprising incorporating stearic acid in an amount more than 0.1% and less than 1% by weight relative to the weight of the pharmaceutical composition comprising olmesartan medoxomil, wherein each of the constituents being incorporated into said composition has a pH less than 8 if measured by a glass electrode in an aqueous solution or suspension containing 1 g of said constituents in 100 g of water at room temperature and wherein said olmesartan medoxomil has a particle size of $d0.9<140$ μm.

24. A stabilized pharmaceutical composition comprising:
    4-10% by weight olmesartan medoxomil having a particle size wherein $d(0.9)$ is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid, wherein olmesartan medoxomil and olmesartan medoxomil degradation products comprising olmesartan acid are the only active ingredients in the pharmaceutical composition, wherein said composition is optionally coated, and wherein each of the constituents being incorporated into said composition has a pH less than 8 if measured by a glass electrode in an aqueous solution or suspension containing 1 g of said constituents in 100 g of water at room temperature, and wherein the amount of olmesartan acid does not increase more than 0.3% if exposed to 75% relative humidity at 40° C. in an open dish for one month.

25. A stabilized pharmaceutical composition in the form of a tablet core, pellet or granule comprising: olmesartan medoxomil having a particle size wherein $d(0.9)$ is less than 140 μm in an amount of from 2% to 20% by weight, stearic acid in an amount below 1% by weight of the composition, and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein each of the constituents being incorporated into said composition has a pH less than 8 if measured by a glass electrode in an aqueous solution or suspension containing 1 g of said constituents in 100 g of water at room temperature, and
- wherein the amount of olmesartan acid does not increase more than 0.3% if exposed to 75% relative humidity at 40° C. in an open dish for one month.

26. A process for making a stabile pharmaceutical composition comprising olmesartan medoxomil having a particle size of d0.9<140 μm, and stearic acid in an amount of from 0.1 to 1% by weight of the composition, where each of the constituents being incorporated into a composition has a pH less than 8 if measured by a glass electrode in an aqueous solution or suspension containing 1 g of said constituents in 100 g of water at room temperature and wherein the pharmaceutical composition is coated with a coating where an aqueous solution or suspension containing 1 g of coating in 100 g of water at room temperature has a pH less than 8 if measured by a glass electrode.

27. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein said composition is optionally coated, and
- wherein when exposed to 75% relative humidity at 40° C. in an open dish for one month, the total amount of related substances does not increase more than 1% and the amount of olmesartan acid does not increase more than 0.3%,
- wherein each of the constituents being incorporated into said composition has a pH less than 8 if measured by a glass electrode in an aqueous solution or suspension containing 1 g of said constituents in 100 g of water at room temperature.

28. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein said composition is optionally coated,
- wherein when exposed to 75% relative humidity at 40° C. in an open dish for one month the total amount of related substances increases from a starting amount of 0.2-0.6% by weight to not more than 0.5-1.4% by weight, and the amount of olmesartan acid does not increase more than 0.3%,
- wherein each of the constituents incorporated into said composition has a pH less than 8 if measured by a glass electrode in an aqueous solution or suspension containing 1 g of said constituents in 100 g of water at room temperature.

29. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein said composition is optionally coated,
- wherein each of the constituents incorporated into said composition has a pH less than 8 if measured by a glass electrode in an aqueous solution or suspension containing 1 g of said constituents in 100 g of water at room temperature, and wherein when the pharmaceutical composition is exposed to 75% relative humidity at 40° C. in an open dish for one month the amount of olmesartan acid does not increase more than 0.3%.

30. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein said composition is optionally coated,
- wherein each of the constituents being incorporated into said composition has a pH less than 8 if measured by a glass electrode in an aqueous solution or suspension containing 1 g of said constituents in 100 g of water at room temperature, and
- wherein when the pharmaceutical composition is exposed to 75% relative humidity at 40° C. in an open dish for one month the amount of olmesartan acid increases from a starting amount of 0.05-0.2% by weight to not more than 0.2-0.5% by weight.

31. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid,
- wherein olmesartan medoxomil and olmesartan medoxomil degradation products comprising olmesartan acid are the only active ingredients in the pharmaceutical composition,
- wherein said composition is optionally coated,
- wherein each of the constituents being incorporated into said composition has a pH less than 8 if measured by a glass electrode in an aqueous solution or suspension containing 1 g of said constituents in 100 g of water at room temperature, and wherein when the pharmaceutical composition is exposed at room temperature to 100% relative humidity for 3 days, thereafter sealed and stored at 60° C. for one week, the amount of olmesartan acid does not increase more than 0.3%.

32. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid, wherein olmesartan medoxomil and olmesartan medoxomil degradation products comprising olmesartan acid are the only active ingredients in the pharmaceutical composition, wherein each of the constituents being incorporated into said composition has a pH less than 8 if measured by a glass electrode in an aqueous solution or suspension containing 1 g of said constituents in 100 g of water at room temperature, wherein said composition is optionally coated, wherein when the pharmaceutical composition is exposed at room temperature to relative humidity 100% for 3 days, thereafter sealed and stored at 60° for one week, the amount of olmesartan acid increases from a starting amount of 0.05-0.2% by weight to not more than 0.5-1.0% by weight, and wherein when exposed to 75% relative humidity at 40° C. in an open dish for one month, the amount of olmesartan acid does not increase more than 0.3%.

33. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid, wherein olmesartan medoxomil and olmesartan medoxomil degradation products comprising olmesartan acid are the only active ingredients in the pharmaceutical composition, wherein said composition is optionally coated, wherein each of the constituents incorporated into said composition has a pH less than 8 if measured by a glass electrode in an aqueous solution or suspension containing 1 g of said constituents in 100 g of water at room temperature, and wherein when the pharmaceutical composition is sealed and stored at 60° C. for one week, the amount of olmesartan acid does not increase more than 0.2%.

34. A pharmaceutical composition comprising: 4-10% by weight olmesartan medoxomil having a particle size wherein d(0.9) is less than 140 μm; 45-55% by weight lactose monohydrate; 15-25% by weight microcrystalline cellulose; 10-20% by weight low-substituted hydroxypropylcellulose; more than 0.1% and less than 1% by weight stearic acid; and olmesartan medoxomil degradation products comprising olmesartan acid, wherein olmesartan medoxomil and olmesartan medoxomil degradation products comprising olmesartan acid are the only active ingredients in the pharmaceutical composition, wherein said composition is optionally coated, wherein each of the constituents incorporated into said composition has a pH less than 8 if measured by a glass electrode in an aqueous solution or suspension containing 1 g of said constituents in 100 g of water at room temperature, and wherein when the pharmaceutical composition is sealed and stored at 60° C. for one week, the amount of olmesartan acid increases from the starting amount of 0.05-0.2% by weight to not more than 0.2-0.4% by weight.

* * * * *